United States Patent
Hoecht et al.

(10) Patent No.: US 11,468,982 B2
(45) Date of Patent: Oct. 11, 2022

(54) MEDICAL IMAGING APPARATUS AND METHOD FOR ACTUATING AT LEAST ONE DISPLAY OF A MEDICAL IMAGING APPARATUS

(71) Applicant: Siemens Healthcare GmbH, Erlangen (DE)

(72) Inventors: Philipp Hoecht, Lauf (DE); Harald Karl, Fuerth (DE); Felix Wolf, Erlangen (DE)

(73) Assignee: Siemens Healthcare GmbH, Erlangen (DE)

( * ) Notice: Subject to any disclaimer, the term of this patent is extended or adjusted under 35 U.S.C. 154(b) by 421 days.

(21) Appl. No.: 16/584,637

(22) Filed: Sep. 26, 2019

(65) Prior Publication Data
US 2020/0105410 A1  Apr. 2, 2020

(30) Foreign Application Priority Data

Sep. 28, 2018 (EP) .................................... 18197463

(51) Int. Cl.
*G16H 40/67* (2018.01)
*A61B 6/00* (2006.01)
(Continued)

(52) U.S. Cl.
CPC ............. *G16H 40/67* (2018.01); *A61B 6/461* (2013.01); *G16H 40/20* (2018.01); *H04L 9/40* (2022.05); *H04L 67/025* (2013.01); *H04L 67/1051* (2013.01); *H04L 67/125* (2013.01); *A61B 5/0037* (2013.01); *A61B 5/055* (2013.01); *A61B 6/032* (2013.01); *A61B 6/488* (2013.01); *G01R 33/20* (2013.01); *G06Q 10/06* (2013.01)

(58) Field of Classification Search
CPC ........ G16H 30/00–40; G16H 40/60–67; A61B 5/00–7495; A61B 6/00–589; A61B 8/00–587; A61B 2576/00–026; G01R 33/00–64
See application file for complete search history.

(56) References Cited

U.S. PATENT DOCUMENTS 5,733,247 A * 3/1998 Fallon .................. A61B 5/0017
324/309
6,451,015 B1 * 9/2002 Rittman, III ....... A61B 18/1206
600/523
(Continued)

FOREIGN PATENT DOCUMENTS

WO  WO-2013169687 A1 * 11/2013  ............ A61M 5/007

OTHER PUBLICATIONS

European Search Report dated Jan. 3, 2020, Application No. 19196841.1.

*Primary Examiner* — Glenton B Burgess
*Assistant Examiner* — Julian Chang
(74) *Attorney, Agent, or Firm* — Banner & Witcoff Ltd.

(57) ABSTRACT

A medical imaging apparatus with a medical scanner unit and at least one display is described, as well as a method for actuating at least one display of a medical imaging apparatus. The techniques disclosed are based on a medical imaging apparatus with a medical scanner unit, a computing unit which is connected to a master unit, and at least one display. The at least one display may include a slave unit, and the master unit may be connected to the slave unit by means of a data connection.

20 Claims, 4 Drawing Sheets

(51) Int. Cl.

| | |
|---|---|
| *H04L 67/025* | (2022.01) |
| *A61B 5/00* | (2006.01) |
| *G16H 40/20* | (2018.01) |
| *H04L 67/125* | (2022.01) |
| *H04L 67/104* | (2022.01) |
| *H04L 9/40* | (2022.01) |
| *A61B 5/055* | (2006.01) |
| *A61B 6/03* | (2006.01) |
| *G06Q 10/06* | (2012.01) |
| *G01R 33/20* | (2006.01) |

(56) References Cited

U.S. PATENT DOCUMENTS

| | | | | |
|---|---|---|---|---|
| 6,483,503 | B1* | 11/2002 | Spannaus | G06T 1/20 345/546 |
| 8,307,401 | B1* | 11/2012 | Lida | G06F 13/4269 725/80 |
| 8,725,801 | B2* | 5/2014 | Kariathungal | G16H 40/63 709/204 |
| 10,045,696 | B2* | 8/2018 | Mackie | G02B 21/008 |
| 10,278,779 | B1* | 5/2019 | Rudie | A61B 34/20 |
| 10,520,797 | B2* | 12/2019 | Yamamoto | H04N 9/3155 |
| 10,786,218 | B2* | 9/2020 | Fukuyo | A61B 6/52 |
| 10,936,879 | B2* | 3/2021 | Ibrahim | B64D 45/00 |
| 11,194,537 | B2* | 12/2021 | Okada | G09G 3/001 |
| 2001/0035752 | A1 | 11/2001 | Kormos et al. | |
| 2003/0066537 | A1* | 4/2003 | Fabian | A61B 5/06 128/899 |
| 2005/0075688 | A1* | 4/2005 | Toy | A61N 1/37235 607/60 |
| 2005/0075691 | A1* | 4/2005 | Phillips | A61N 1/37235 607/60 |
| 2005/0075692 | A1* | 4/2005 | Schommer | A61N 1/37235 607/60 |
| 2005/0124866 | A1* | 6/2005 | Elaz | A61M 16/0051 128/920 |
| 2005/0133027 | A1* | 6/2005 | Elaz | A61B 5/002 128/200.24 |
| 2005/0143632 | A1* | 6/2005 | Elaz | G16Z 99/00 600/301 |
| 2006/0030338 | A1* | 2/2006 | Harken | H04W 88/02 455/456.6 |
| 2006/0241384 | A1* | 10/2006 | Fisher | A61B 5/0013 600/414 |
| 2006/0247529 | A1* | 11/2006 | Rose | A61B 8/12 600/466 |
| 2006/0277073 | A1* | 12/2006 | Heilbrunn | G16H 15/00 705/3 |
| 2007/0016034 | A1* | 1/2007 | Donaldson | A61B 8/0833 600/437 |
| 2007/0043597 | A1* | 2/2007 | Donaldson | A61B 8/565 705/3 |
| 2007/0066882 | A1* | 3/2007 | Maschke | A61B 5/06 600/407 |
| 2007/0127791 | A1* | 6/2007 | Ernvik | G16H 50/50 382/128 |
| 2008/0125643 | A1* | 5/2008 | Huisman | A61B 5/14546 600/420 |
| 2009/0016483 | A1* | 1/2009 | Kawasaki | A61B 6/504 378/4 |
| 2009/0094658 | A1* | 4/2009 | Kobayashi | H04N 7/163 725/118 |
| 2009/0182917 | A1* | 7/2009 | Kim | G06F 3/1438 710/106 |
| 2009/0203999 | A1* | 8/2009 | Rust | A61B 8/565 600/443 |
| 2009/0259121 | A1* | 10/2009 | Simonetti | A61B 5/0044 482/54 |
| 2009/0278763 | A1* | 11/2009 | Zeng | G06F 3/1431 345/1.1 |
| 2009/0322767 | A1* | 12/2009 | Douglas | G09G 5/006 345/520 |
| 2009/0326389 | A1* | 12/2009 | Ralfs | A61B 5/0205 128/204.23 |
| 2010/0036236 | A1* | 2/2010 | Fisher | A61B 5/002 600/411 |
| 2010/0312096 | A1* | 12/2010 | Guttman | A61B 34/25 600/411 |
| 2011/0216245 | A1* | 9/2011 | Kyriazis | G06F 3/1431 348/723 |
| 2011/0230755 | A1* | 9/2011 | MacFarlane | G06T 7/246 600/414 |
| 2011/0237960 | A1* | 9/2011 | Rantala | A61B 5/055 600/300 |
| 2011/0254876 | A1* | 10/2011 | Yokoyama | G06F 3/1446 345/690 |
| 2011/0257509 | A1* | 10/2011 | Olsen | A61N 1/37235 600/411 |
| 2012/0010475 | A1* | 1/2012 | Rossmeier | A61B 6/463 600/301 |
| 2012/0062800 | A1* | 3/2012 | Sisto | G09G 5/006 348/660 |
| 2012/0089006 | A1* | 4/2012 | Ren | A61B 5/055 600/410 |
| 2012/0133601 | A1* | 5/2012 | Marshall | G06F 3/04817 345/173 |
| 2013/0159401 | A1* | 6/2013 | Sukeno | G09G 5/008 709/203 |
| 2013/0181884 | A1* | 7/2013 | Perkins | G06F 3/1423 345/1.3 |
| 2013/0235969 | A1* | 9/2013 | Winter | A61N 5/1079 378/4 |
| 2013/0295984 | A1* | 11/2013 | Todoroki | H04B 7/026 455/550.1 |
| 2013/0328745 | A1* | 12/2013 | Koltuk | G06F 3/1446 345/1.3 |
| 2014/0037068 | A1* | 2/2014 | Burion | A61B 34/25 378/95 |
| 2014/0078399 | A1* | 3/2014 | Frouin | H01Q 21/28 348/516 |
| 2014/0111530 | A1* | 4/2014 | Choi | G06F 12/00 345/545 |
| 2014/0128881 | A1* | 5/2014 | Tyc | A61B 18/1492 606/20 |
| 2014/0152784 | A1* | 6/2014 | McCoy | H04N 13/167 348/52 |
| 2014/0180083 | A1* | 6/2014 | Hoseit | A61B 5/0084 600/431 |
| 2014/0275954 | A1* | 9/2014 | Ohta | G06F 30/20 600/407 |
| 2014/0276056 | A1* | 9/2014 | Ohta | A61B 1/00011 600/407 |
| 2014/0347251 | A1* | 11/2014 | Cho | G16H 40/67 345/2.3 |
| 2015/0187333 | A1* | 7/2015 | Loeffler | G09G 5/04 345/1.3 |
| 2015/0269912 | A1* | 9/2015 | Chen | G06F 3/1446 345/699 |
| 2015/0366454 | A1* | 12/2015 | Zeng | G01J 3/44 362/249.02 |
| 2016/0027146 | A1 | 1/2016 | Kim et al. | |
| 2016/0119507 | A1* | 4/2016 | Duyvejonck | H04N 9/3147 348/512 |
| 2016/0157803 | A1* | 6/2016 | Keller | A61B 8/12 600/467 |
| 2017/0094166 | A1* | 3/2017 | Riedel | H04N 7/181 |
| 2017/0132987 | A1* | 5/2017 | Kato | H04N 21/4307 |
| 2017/0220748 | A1* | 8/2017 | Okabe | G16H 30/40 |
| 2017/0332148 | A1* | 11/2017 | Fullerton | H04L 12/4625 |
| 2017/0339379 | A1* | 11/2017 | Tanaka | H04N 9/3155 |
| 2018/0042517 | A1* | 2/2018 | van der Weide | A61B 5/064 |
| 2018/0367768 | A1* | 12/2018 | Nobori | H04N 9/3194 |
| 2019/0121594 | A1* | 4/2019 | Akiyama | G09G 5/14 |
| 2019/0122633 | A1* | 4/2019 | Pan | G09G 5/005 |
| 2019/0142519 | A1* | 5/2019 | Siemionow | A61B 5/7267 600/408 |
| 2019/0205080 | A1* | 7/2019 | Tsubaki | H04N 21/436 |
| 2019/0231229 | A1* | 8/2019 | Sturgeon | G06F 3/041 |

(56) References Cited

U.S. PATENT DOCUMENTS

| | | | | |
|---|---|---|---|---|
| 2019/0377535 A1* | 12/2019 | Rycyna | .................. | H04L 12/28 |
| 2019/0394454 A1* | 12/2019 | Katsuki | ................ | H04N 13/385 |
| 2020/0046450 A1* | 2/2020 | Tsao | .......................... | F15B 7/00 |
| 2020/0084491 A1* | 3/2020 | Asnis | ................... | H04N 21/816 |
| 2020/0275225 A1* | 8/2020 | Proctor, Jr. | ........ | H04N 21/8106 |
| 2021/0195282 A1* | 6/2021 | Lu | ....................... | H04N 21/8458 |
| 2021/0343377 A1* | 11/2021 | Kobneck | ................ | G16H 30/40 |

* cited by examiner

MEDICAL IMAGING APPARATUS AND METHOD FOR ACTUATING AT LEAST ONE DISPLAY OF A MEDICAL IMAGING APPARATUS

CROSS-REFERENCE TO RELATED APPLICATIONS

The present application claims the benefit of the filing date of European patent application no. EP18197463.5, filed on Sep. 28, 2018, the contents of which are incorporated herein by reference in their entirety.

TECHNICAL FIELD

The present disclosure relates to a medical imaging apparatus with a medical scanner unit, a computing unit, a master unit which is connected to the computing unit, and at least one display. Furthermore, the disclosure is based on a method for actuating at least one display of a medical imaging apparatus.

BACKGROUND

Medical imaging apparatuses often have a display, which may be arranged directly on a scanner unit of the medical imaging apparatus or in the vicinity of the scanner unit. The scanner unit (and therefore the display) are situated within an examination room. A control computer, such as a computing unit for example, is by contrast usually arranged in a control room. The display is linked to the control computer, in particular to the computing unit, via a data connection.

If the medical imaging apparatus is formed by a magnetic resonance apparatus, for example, then the data connection between the display unit and the control computer must also take place via fiber optic cables. Using copper cables is problematic due to electric fields which may be generated by the copper cables, since these electric fields may influence magnetic resonance imaging. Moreover, if the magnetic resonance apparatus has more than one display, then it has been previously necessary to use a dedicated data connection, such as a dedicated fiber optic connection, to the control computer for each individual display. For this purpose, the individual displays must also have a fiber optic transducer and/or fiber optic converter so that the signal can be transferred from the fiber optic cable to the display.

Currently available implementations for a fiber optic transfer are not particularly robust, however, meaning that this may lead to connection problems between the individual displays and the control computer, in particular the computing unit. Additionally, fiber optic transducers and/or fiber optic converters are also susceptible to interference when the individual displays are frequently switched on or off. In addition, displays that are connected to a control computer by means of a DisplayPort frequently first have to be identified after each time they are switched on, and subsequently a link training has to be performed, which is very time consuming. The individual displays need to be switched off during a magnetic resonance examination so that the electronics of the displays do not cause any interference in magnetic resonance image data.

SUMMARY

The present disclosure is based on the object of enabling a secure and robust data transfer between a computing unit and a display arranged within an examination room. The object is achieved with the features of the independent claims. Further advantageous embodiments are described in the dependent claims and throughout the disclosure.

The disclosure is based on a medical imaging apparatus with a medical scanner unit, a computing unit, a master unit which is connected to the computing unit, and at least one display. In this context, it may be provided that the at least one display comprises a slave unit, wherein the master unit is connected to the slave unit by means of a data connection of the medical imaging apparatus.

The medical imaging apparatus may be formed by any suitable type of medical imaging apparatuses that appear expedient to the person skilled in the art, such as for example an X-ray apparatus, a PET apparatus (Positron Emission Tomography apparatus), etc. Advantageously, the medical imaging apparatus may be formed by a magnetic resonance apparatus, since a simple and secure data transfer between the computing unit and the display can be provided here due to the master-slave relationship. In addition, in a magnetic resonance apparatus, the disclosure allows the display to be switched off during the magnetic resonance scan and quickly switched on again thereafter, so as to not generate any electromagnetic artifacts during the scan.

The scanner unit of the medical imaging apparatus is designed to capture medical image data during a medical imaging examination. To this end, the scanner unit may be arranged in an examination room. The scanner unit may, for example, comprise a magnet unit, an X-ray detector, etc. In an embodiment, the at least one display of the medical imaging apparatus is also arranged within the examination room. The computing unit, by contrast, is arranged together with the master unit in a control room, and the control room is embodied separately from the examination room. The examination room is embodied so as to be decoupled from the control room with regard to an exchange of electromagnetic radiation.

The computing unit is designed to control the medical imaging apparatus. To this end, the computing unit may access the required software and/or computer programs, which are stored in a memory. In this context, the memory may be comprised by the computing unit or may also be embodied separately from the computing unit. The memory may also be comprised by the medical imaging apparatus or may be formed by an external memory. The computer programs and/or software may be executed in a processor of the computing unit, and when the computer programs and/or software are executed, the medical imaging apparatus may be controlled to perform the various embodiments as discussed herein.

The at least one display may comprise a monitor and/or a touch display arranged within the examination room. In this context, the at least one display may be arranged directly on the scanner unit, such as on a front side of the scanner unit and/or on a patient couch of the scanner unit for example. The medical imaging apparatus may have a single display or two or more displays in this context, which are arranged within the examination room. In an embodiment, each of the displays has a dedicated slave unit for communication with the master unit. In addition, the at least one display, which may comprise a monitor and/or a touch display, may also be arranged within an operator room. The at least one display and the master unit may be arranged in different rooms.

The master unit may comprise a unit, by means of which the access to a resource can be regulated. To this end, the master unit has a logic unit and/or a logic circuit, such as an FPGA (Field Programmable Gate Array) for example, which regulates the individual access rights. Here, the logic unit and/or the logic circuit regulates the access rights for the slave unit of the at least one display to the transferred data. In this context, the logic unit and/or the logic circuit may have a programmable and/or configurable FPGA. In an embodiment, the logic unit and/or the logic circuit may have a reprogrammable and/or reconfigurable FPGA. Continuing this example, the transfer protocol for the slave unit of the at least one display may be generated in the logic unit and/or the logic circuit of the master unit. The transfer protocol comprises data, which is provided for actuating the individual displays and for representing display data by means of the individual display. The logic unit (e.g. the FPGA) comprises a SerDes (serializer/deserializer), which comprises a serial interface. Thus, the transfer protocol may alternatively be referred to as transfer data or transfer protocol data.

In this context, the master unit may comprise a unit which is embodied separately from the computing unit. Alternatively, the master unit may be comprised by the computing unit or also be integrated in the computing unit.

The slave unit of the at least one display, by contrast, receives its access rights from the master unit. To this end, the slave unit of the at least one display may likewise have a logic unit and/or a logic circuit, such as an FPGA for example, to execute and/or implement the received protocol (e.g. the received transfer protocol) correctly within the display. In an embodiment, when generating the transfer protocol within the master unit (e.g. within the logic unit) standard image data is already transferred into the transfer protocol.

The data connection may comprise a connection between the master unit and the slave unit of the at least one display. By means of the data connection, the transfer protocol (e.g. a Human Machine Interface Net (HMINet) protocol), can be transferred from the master unit to the slave unit of the at least one display and/or from the slave unit of the at least one display to the master unit. The data connection may be formed by any suitable type of data connections which appear expedient to the person skilled in the art.

In an embodiment, it is advantageously possible to dispense with standard interfaces with signal transducers during the data transfer from the computing unit to at least one display within the examination room. Standard interfaces of this kind may, for example, comprise one or more of a Digital Visual Interface (DVI), a DisplayPort interface, a Universal Serial Bus interface (USB interface), etc. Standard interfaces of this kind with the signal transducers associated therewith (e.g. signal transducers for converting an electrical signal into a fiber optic signal and back again), are susceptible to interference, and thus may lead to a data transfer being disrupted and/or impaired.

Thus, on the basis of the embodiments of the present disclosure, by contrast, it is possible for a robust implementation of a connection between the computing unit (e.g. the master unit), and a display, which is arranged within the examination area, to be provided. In this context, the data connection may be linked to the master unit and/or to the slave unit directly, so that it is possible to dispense with additional signal transducers. In addition, in this context different standard image signals and/or standard image data and/or control data for actuating the at least one display by means of a data connection may be exchanged between the master unit and the slave unit.

By using an HMINet protocol, it is additionally possible for a DisplayPort to only be terminated in the HMINet of the master unit, i.e. from the perspective of a host PC, which comprises a user interface, the display is always on. Thus, only the master unit learns or becomes aware of the switching-off or shutdown of the displays. The connection of master unit to slave unit is optimized in such a way that a rapid switching-on is possible. This is achieved in that pixel data, which actuates the display, is transferred directly and the connection is re-established very rapidly.

In an advantageous development of the medical imaging apparatus embodiments discussed herein, it may be provided that the data connection comprises an optical data connection between the slave unit and the master unit. The optical data connection may comprise optical waveguides or fiber optic cables, for example. In addition, the optical data connection may comprise an optical high-speed data connection, such as by means of high-speed fiber optics, for example. This means that, in magnetic resonance apparatuses in particular, an interference-free operation, in particular an interference-free capturing of magnetic resonance image data, is achieved. Additionally, it is advantageously possible to avoid using copper conductors and/or electrical conductors within the examination room and thus also avoid impairing a magnetic resonance examination due to the copper conductors and/or the electrical conductors.

In an advantageous development of the medical imaging apparatus embodiments discussed herein, it may be provided that the data connection comprises a bidirectional data connection. This means that both a data transfer from the master unit to the slave unit of the at least one display and/or from the slave unit of the at least one display to the master unit take place.

In an advantageous development of the medical imaging apparatus embodiments discussed herein, it may be provided that the master unit has a logic unit, by means of which a transfer protocol can be generated. When generating the transfer protocol, it is possible for standard image signals to be converted, for example. Standard image signals may comprise image signals, for example, which may be transferred by one or more of Universal Serial Bus (USB) protocols (e.g., USB 2.x, USB 3.x, etc.), by Inter-Integrated Circuit (I2C) protocols, by DisplayPort protocols, by Low Voltage Differential Signaling (LVDS) protocols, etc. The logic unit and/or the logic circuit may comprise a programmable and/or configurable FPGA. Furthermore, the logic unit and/or the logic circuit may have a reprogrammable and/or reconfigurable FPGA, with the FPGA being configured and/or programmed such that standard image signals and/or control signals for the at least one display are converted before the data transfer to the slave unit. In this manner, it is possible for the corresponding signals to be already converted within the master unit. This enables a particularly robust and/or stable data connection for data transfer between the master unit and the slave unit. In addition, it is advantageously possible to dispense with additional signal transducers.

In particular, the modular units and/or components of the master unit may be programmable logic units, such as reprogrammable logic units, meaning that a simple adaptation to new standards and/or requirements can take place by a new programming of the logic units. Thus, it is advantageously also possible to avoid exchanging the units (e.g. the hardware units). In addition, the logic units may also comprise universally programmable logic units, which simplifies an exchange of logic units. This means that a universally programmable module (e.g. the logic unit), can be simply exchanged with another universally programmable module (e.g. the logic unit), of the master unit.

In an advantageous development of the medical imaging apparatus embodiments discussed herein, it may be provided that the at least one slave unit comprises a logic unit, by means of which a transfer protocol can be executed. The logic unit may comprise an FPGA, which is configured and/or programmed such that the transfer protocol (e.g. the HMINet protocol), is transferred into control signals for the at least one display and/or into standard image signals for display interfaces, such as LVDS, I2C, USB, etc. For example, the LVDS interface may be used for LVDS data and/or LVDS signals for output to an LCD panel and/or actuation of an LCD panel of the at least one display, etc. The I2C interface may for example be used for I2C data and/or the I2C signals may be used for output to a touch controller and/or actuation of a touch controller of the at least one display, etc. Such embodiments enable execution of the transfer protocol, and thus a manner to provision display data and/or control data for the at least one display. In addition, it is advantageously also possible to dispense with additional signal transducers.

In an embodiment, the modular units of the slave unit comprise programmable logic units, in particular reprogrammable logic units, meaning that an adaptation to new standards and/or requirements can take place by a new programming of the logic units. This means that it is advantageously also possible to avoid exchanging the units (e.g. the hardware units). In addition, the logic units may also comprise universally programmable logic units, which simplifies an exchange of logic units. This means that a universally programmable module (e.g. the logic unit), can be exchanged with another universally programmable module (e.g. the logic unit), of the slave unit.

In an advantageous development of the medical imaging apparatus embodiments discussed herein, it may be provided that the slave unit of the at least one display comprises an interface for relaying the received control signals and/or display data. By means of the interface, it is possible for control signals and/or display data, for example, to be relayed and/or forwarded via an LVDS interface to an LCD panel of the at least one display. In addition, by means of the interface, for example, data can be relayed and/or forwarded via an I2C interface to a touch panel and/or a touch controller of the display.

In an advantageous development of the medical imaging apparatus embodiments discussed herein, it may be provided that the at least one display has a transceiver unit and the master unit has a transceiver unit. The transceiver unit may be configured for sending and/or receiving data and/or signals. The data connection between the master unit and the display may be arranged between the transceiver unit of the master unit and the transceiver unit of the at least one display. The transceiver unit of the display may be coupled to the slave unit of the display directly and/or comprised by the slave unit. Advantageously, the transceiver unit of the master unit and/or the transceiver unit of the display may comprise a fiber optic transceiver unit. This means that an advantageous transfer of a transfer protocol (e.g. an HMINet protocol), may take place between the master unit and the at least one display, which is arranged within the examination room.

In an advantageous development of the medical imaging apparatus embodiments discussed herein, it may be provided that the display is formed by a first display, with the medical imaging apparatus comprising at least one further display with a slave unit. In this context, the medical imaging apparatus may comprise a single further display or also two or more further displays. In this context, each of the further displays may comprise a dedicated slave unit with a logic unit (e.g. an FPGA). In this manner, a simple data transfer can take place between the computing unit and the individual displays. In this manner, it is also possible for an allocation of control data and/or display data for the respective display to take place by means of the master unit.

The logic unit of the master unit (e.g. the FPGA), may be configured such that a transfer protocol of any suitable number (e.g., up to four) displays of the medical imaging apparatus can be generated by means of a single FPGA. It is also possible for the transfer protocol for a plurality of displays to be transferred to the displays by means of a data connection, such as a single data connection, for instance. If the medical imaging apparatus comprises more than four displays, for example, then it may be provided that more than one single FPGA is arranged within the logic unit or also that the logic unit has further units, which can generate a transfer protocol for more than four displays of the medical imaging apparatus.

In an advantageous development of the medical imaging apparatus embodiments discussed herein, it may be provided that the medical imaging apparatus has a number n of displays, with n≥2 and with the (n−1)th display having a transceiver unit for a data connection with the n-th display. In this context, the transfer protocol may comprise information relating to the control data and/or display data of the n-th display, and also relating to the control data and/or display data of the (n−1)th display. For instance, in this context it is possible for the control data and/or display data for the n-th data to be looped through on the (n−1)th display by means of the transfer protocol. Advantageously, in this context it is possible for data connections between the master unit and the individual displays (and thus also between the control room and the examination room) to be reduced to a minimum.

In an advantageous development of the medical imaging apparatus embodiments discussed herein, it may be provided that each (n−1)th display has a first transceiver unit for input of the transfer protocol and a second transceiver unit for forwarding the transfer protocol. In accordance with such embodiments, the first transceiver unit of the first display may be provided for input and/or receiving of the transfer protocol directly from the master unit or from the (n−2)th display. The second transceiver unit may be provided for forwarding the transfer protocol to a further display (e.g. the n-th display). In this manner, it is possible by means of the transfer protocol for the control data and/or display data for a plurality of displays to be transferred by means of a data connection (e.g. a single data connection), and looped through at the previously-connected display, until the transfer protocol has reached the destination (e.g. one of the n displays). Advantageously, in this context it is likewise possible for data connections between the master unit and the individual displays (and thus also between the control room and the examination room) to be reduced to a minimum.

In an advantageous development of the medical imaging apparatus embodiments discussed herein, it may be provided that an operating mode of the n-th display is at least partially dependent upon an operating mode of the (n−1)th display. In this context, an operating mode of a display is understood as meaning an inactive operating mode and/or operating state of the display, or also an active operating mode and/or operating state of the display. The inactive state may, for example, comprise a switched-off state of the display or also a standby state of the display. The active state may comprise a state in which the display is in a switched-on state and displays data. In medical imaging examinations, which are formed by a magnetic resonance examination, it is advantageous that the individual displays within the examination room are switched off during the medical imaging examination, so as to not impair or interfere with the medical imaging examination (e.g. a magnetic resonance examination). Thus, a simple switching-off of the display (or also a simple and rapid disabling of the display within the examination room) can be achieved, since, for example, only the first display along the data transfer chain has to be disabled or switched off to also disable the further-connected displays.

In an embodiment, a disabling and/or deactivation of the individual displays, such as a shutdown for example, takes place automatically by means of the computing unit, such as during a medical imaging examination for example, so that interference can be advantageously prevented by the display during the medical imaging examination (e.g. for capturing of magnetic resonance image data). The deactivation or shutdown of the individual displays can be detected by the master unit here.

In an advantageous development of the medical imaging apparatus embodiments discussed herein, it may be provided that the master unit comprises a first transceiver unit for transferring a transfer protocol to the at least one display, and a second transceiver unit for transferring a further transfer protocol to a further unit, which comprises a slave unit. The further unit may comprise any suitable unit that appears expedient to the person skilled in the art. For instance, the further unit may comprise a further display. In this manner it is also possible, for instance, for two different transfer protocols to be available for representation by means of the different displays within the examination room. Additionally, the further unit may also comprise a USB interface for linking a USB-capable device.

In an advantageous development of the medical imaging apparatus embodiments discussed herein, it may be provided that the master unit comprises an Ethernet module. By means of the Ethernet module, it is possible for a simpler and more rapid access to the logic unit (e.g. the FPGA), to be provided for a user. For example, by means of the Ethernet module, it is possible for an Ethernet-based diagnosis of the master unit (e.g. the FPGA of the master unit), to take place. In addition, updates for the individual units of the master unit (or also updates for the individual displays or slave units) can be carried out. The Ethernet module may, for example, have an Ethernet connection between a microcontroller for example, which is arranged within the master unit for a configuration and/or implementation of the logic unit for example, and the logic unit (e.g. the FPGA), and a USB interface. By means of the USB interface, for example, a connection can be established between the master unit and a host PC, which may include a user interface. Again, in this context, the USB interface may comprise any suitable USB protocol such as a USB2.0 protocol, a USB3.0 protocol, etc.

In an advantageous development of the medical imaging apparatus embodiments discussed herein, it may be provided that the medical imaging apparatus has a central host PC, which is arranged within a control room together with the master unit. The central host PC may comprise a user interface with an input unit and an output unit. The central host PC may advantageously be comprised by the computing unit. By means of the central host PC, a configuration and/or implementation of the master unit can take place on the part of a user or a configuration and/or implementation of the master unit can also be monitored by a user. In addition, by means of the central host PC, a configuration and/or implementation of the transfer protocol can take place on the part of a user or a configuration and/or implementation of the transfer protocol can also be monitored by a user. Furthermore, by means of the central host PC, a connection diagnosis between the master unit and the displays and/or between the individual displays can be created and/or shown to a user. In this manner, it is also possible for a network management to be enabled for the master unit.

In an advantageous development of the medical imaging apparatus embodiments discussed herein, it may be provided that the master unit has at least one standardized data interface and/or graphical interface for a data exchange with the central host PC. This means that, advantageously, a direct connection can be provided between the master unit and the host PC. This also enables a simple configuration and/or implementation of the master unit and/or the transfer protocol.

The present disclosure makes it possible for a universal interface converter to be made available, to couple the slave unit to the master unit bidirectionally, but to decouple the slave unit from the host PC, which comprises the user interface. In this context, the universal interface converter may comprise standard interfaces (e.g. DisplayPort, USB, Ethernet, Thunderbolt, etc.). The host PC may be connected only to the master unit. As a result, input data on the display, such as touch data in the form of I2C data and/or SPI data for example, can be transferred via the slave unit to the master unit (e.g. to a microcontroller of the master unit), where it is converted to USB. The converted data can then be relayed to the host PC via a standard USB interface. The host PC may, in an embodiment, obtain data from the master unit via the standard USB interface.

Furthermore, the disclosure includes a method for actuating at least one display of a medical imaging apparatus, with the following steps: (1) Providing a transfer protocol within the master unit, (2) Transferring the transfer protocol to the slave unit of the at least one display by means of the data connection, and (3) Executing the transfer protocol in the slave unit.

The medical imaging apparatus may comprise a medical scanner unit, a computing unit, a master unit which is connected to the computing unit, and at least one display. In this context, it may be provided that the at least one display comprises a slave unit, with the master unit being connected to the slave unit by means of a data connection of the medical imaging apparatus. In this context, the master unit may comprise a unit which is embodied separately from the computing unit. Alternatively, the master unit may also be comprised by the computing unit or also be integrated in the computing unit.

By means of the method embodiments according to the disclosure, it is advantageously possible to dispense with standard interfaces with signal transducers during the data transfer from the computing unit to at least one display within the examination room. By means of the present disclosure, it is possible for a robust embodiment of a connection between the computing unit (e.g. the master unit), and a display, which is arranged within the examination area, to be provided. In this context, the data connection may be linked to the master unit and/or to the slave unit directly, so that it is possible to dispense with additional signal transducers. In addition, in this context different standard image signals and/or standard image data and/or control data for actuating the at least one display by means of a data connection may be exchanged between the master unit and the slave unit.

The advantages of the method embodiments according to the disclosure for actuating at least one display of a medical imaging apparatus substantially correspond to the advantages of the medical imaging apparatus according to the disclosure, as described in detail above. Features, advantages, or alternative embodiments discussed with respect to the methods described herein and accompanying claimed method subject matters can likewise also be transferred to the other claimed subject matters and embodiments (e.g. the apparatus embodiments and claimed subject matters), and vice versa.

In an advantageous development of the method embodiments according to the disclosure, it may be provided that the transfer protocol comprises data for a first display and data for at least one further display, with the data for the at least one further display being transferred from the master unit to the slave unit of the first display, and being transferred from the slave unit of the first display to a slave unit of the at least one further display. The data of the transfer protocol may comprise control data and/or display data for the first display and/or control data and/or display data for the at least one further display. In this context, control data and/or display data for the at least one further display may be looped through on the first display by means of the transfer protocol. In addition, in this manner, the transfer protocol (e.g. control data and display data) for a plurality of displays can be transferred and/or transmitted by means of a data connection (e.g. a single data connection), between the master unit and the display. In this context, the transfer protocol (e.g. control data and display data), for a further display is looped through at the previously-connected display, until the transfer protocol has arrived at the destination (e.g. at one of the further displays). Advantageously, in this context it is possible for data connections between the master unit and the individual displays (and thus also between the control room and the examination room) to be substantially reduced or minimized, and therefore for components and costs to be advantageously saved.

In an advantageous development of the method embodiments according to the disclosure, it may be provided that an Ethernet-based evaluation (e.g., processing in accordance with an Ethernet-based protocol) of a connection between the master unit and the at least one display and/or an Ethernet-based network management is carried out. In this manner, it is possible for access to the master unit (e.g. a logic unit of the master unit), to be provided. This access may take place, for instance, together with an Ethernet module of the master unit and a host PC, which has a user interface.

In an advantageous development of the method embodiments according to the disclosure, it can be provided that an automatic shutdown of the at least one display takes place during a medical imaging examination. This enables an advantageous image data capture (e.g. during magnetic resonance examinations), as this means that interference in and/or disruption to the image data capture due to the display can be prevented.

BRIEF DESCRIPTION OF THE DRAWINGS/FIGURES

The accompanying drawings, which are incorporated herein and form a part of the specification, illustrate the embodiments of the present disclosure and, together with the description, further serve to explain the principles of the embodiments and to enable a person skilled in the pertinent art to make and use the embodiments.

The present disclosure is described in detail below using embodiments according to the disclosure with reference to the figures. The exemplary embodiments of the present disclosure will be described with reference to the accompanying drawings. The drawing in which an element first appears is typically indicated by the leftmost digit(s) in the corresponding reference number.

DETAILED DESCRIPTION

Figure 1:
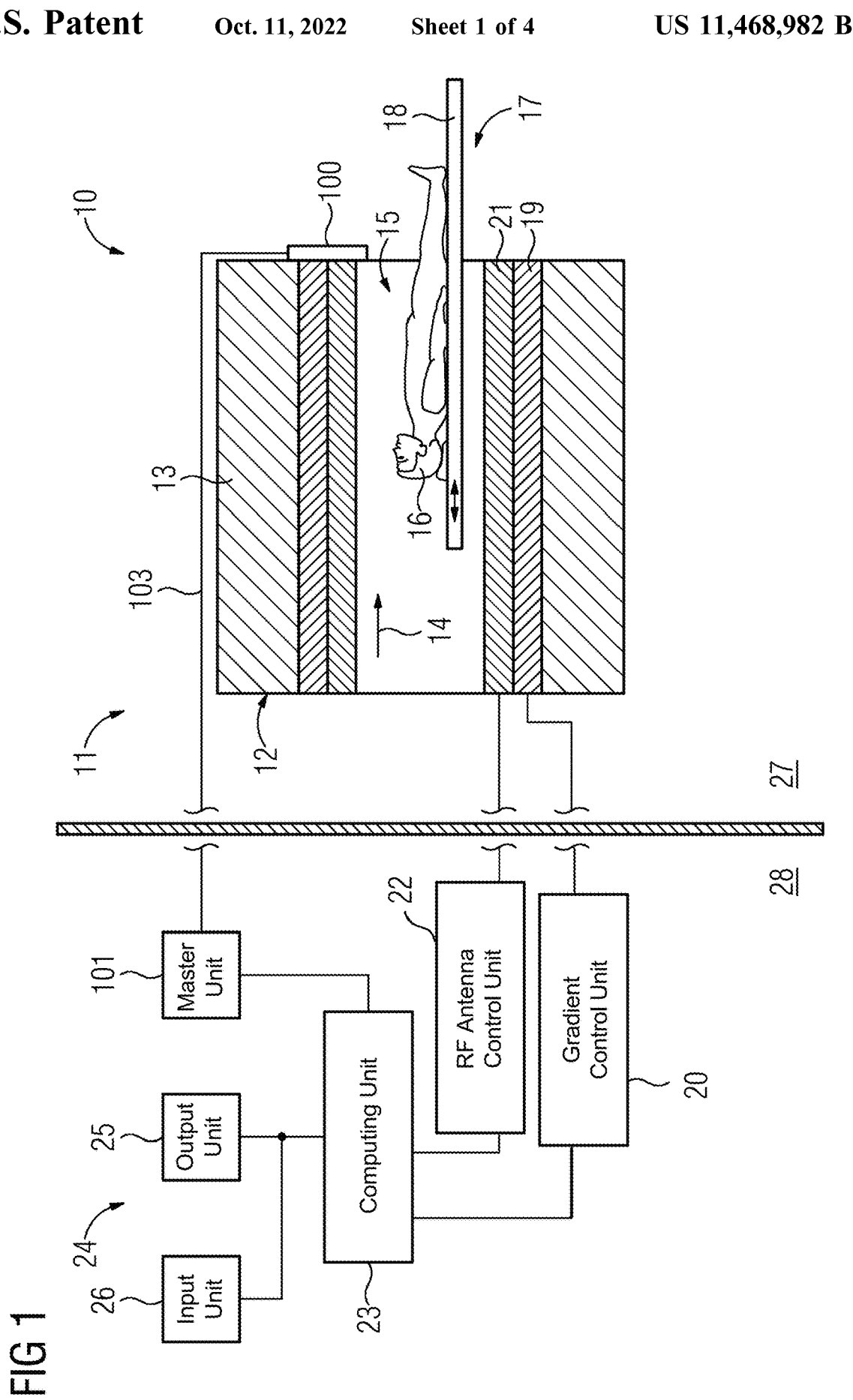
FIG. 1 shows an example schematic representation of a medical imaging apparatus, in accordance with an embodiment of the present disclosure.

FIG. 1 shows an example schematic representation of a medical imaging apparatus, in accordance with an embodiment of the present disclosure. As shown in FIG. 1, a medical imaging apparatus 10 is illustrated schematically. In the present embodiment, the medical imaging apparatus 10 is formed by a magnetic resonance apparatus 11. By way of example the present disclosure is described on the basis of the magnetic resonance apparatus 11. The present disclosure is not, however, restricted to the embodiment of the medical imaging apparatus 10 in conjunction with the magnetic resonance apparatus 11, and further embodiments of the medical imaging apparatus 10, such as an X-ray apparatus, a computed tomography apparatus, a PET apparatus, etc. are readily conceivable.

As shown in FIG. 1, the magnetic resonance apparatus 11 comprises a scanner unit 12 formed by a magnet unit, which comprises a superconducting main magnet 13 for generating a strong and, particularly, constant main magnetic field 14. In addition, the magnetic resonance apparatus 11 has a patient receiving region 15 to accommodate a patient 16. In the present exemplary embodiment, the patient receiving region 15 is embodied in a cylindrical shape and is surrounded cylindrically in a peripheral direction by the magnet unit. In principle, however, it is readily conceivable that the patient receiving region 15 has a different design. The patient 16 can be pushed and/or moved by means of a patient positioning apparatus 17 of the magnetic resonance apparatus 11 into the patient receiving region 15. For this purpose, the patient positioning apparatus 17 has a patient table 18 which is embodied such that it is able to move within the patient receiving region 15.

The scanner unit 12, and in particular the magnet unit, also has a gradient coil unit 19 for generating magnetic field gradients that are used for position encoding during an imaging process. The scanner unit 12 may be alternatively referred to as a data acquisition scanner and, in magnetic resonance imaging embodiments, as a magnetic resonance data acquisition scanner. The gradient coil unit 19 is controlled by means of a gradient control unit 20 of the magnetic resonance apparatus 11. The scanner unit 12, in particular the magnet unit, furthermore comprises a radio-frequency (RF) antenna unit 21 for exciting a polarization which forms in the main magnetic field 14 generated by the main magnet 13. The radio-frequency antenna unit 21 is controlled by a radio-frequency antenna control unit 22 of the magnetic resonance apparatus 11 and radiates radio-frequency magnetic resonance sequences into the patient receiving region 15.

For controlling the main magnet 13, the gradient control unit 20 and, for controlling the radio-frequency antenna control unit 22, the magnetic resonance apparatus 11 has a computing unit 23. The computing unit 23 (e.g. control computer or control processor(s)) centrally controls the magnetic resonance apparatus 11, such as by way of example the performance of a predetermined imaging gradient echo sequence. In addition, the control unit 23 comprises an evaluation unit (not shown in detail) for evaluating medical image data which is captured during the magnetic resonance examination.

The computing unit 23 may be comprises of any suitable number and/or type of processors and/or processing circuitry. To control the magnetic resonance apparatus, the computing unit 23 has computer programs, in particular control programs, and/or software which are saved in a memory unit. In this context, the memory unit may be comprised by the computing unit 23 or may also be embodied separately from the computing unit 23, with the contents of the memory unit being access via the computing unit 23. For example, the memory unit may be comprised by the magnetic resonance apparatus 11 or also may comprise an external memory unit. The controlling of the magnetic resonance apparatus 11 takes place when the computer programs and/or software is/are executed by one or more processors (not shown in detail) of the computing unit 23.

Furthermore, the magnetic resonance apparatus 11 comprises a user interface 24, which is connected to the computing unit 23. Control information, such as imaging parameters for example, as well as reconstructed magnetic resonance images can be displayed on an output unit 25, for example on at least one monitor, of the user interface 24 for medical operating personnel. In addition, the user interface 24 has an input unit 26, by means of which information and/or parameters can be entered during a scanning process by the medical operating personnel.

The scanner unit 12 of the medical imaging apparatus 10 is arranged together with the patient positioning apparatus 17 within an examination room 27. By contrast, the computing unit 23 with the user interface 24 is arranged within a control room 28. The examination room 27 and the control room 28 are embodied separately from one another in this context. For instance, the examination room 27 is embodied so as to be decoupled from the control room 28 with regard to an exchange of electromagnetic radiation, in particular RF radiation.

Figure 2:
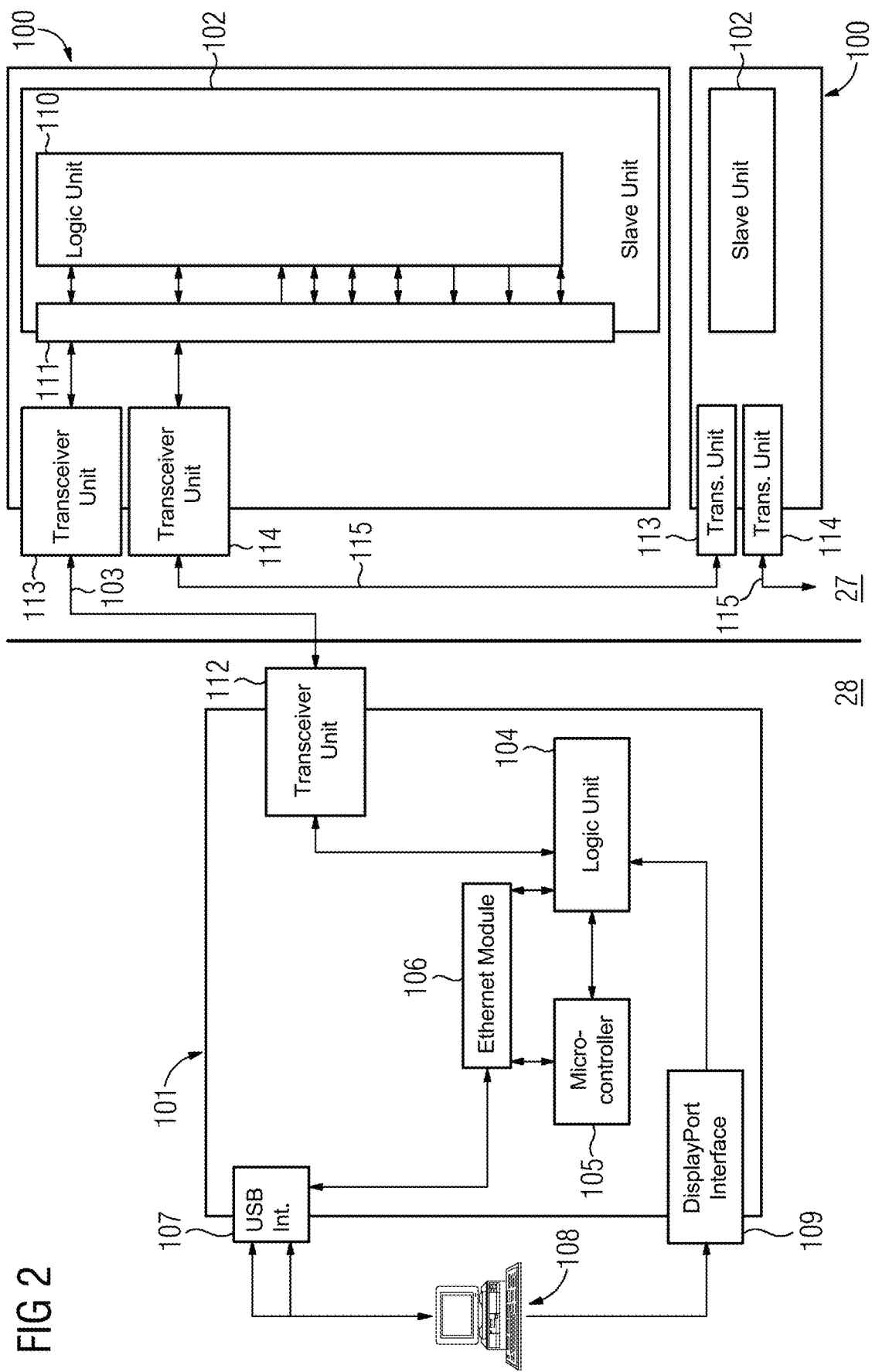
FIG. 2 shows an example schematic representation of a first arrangement of a master unit and a plurality of slave units, in accordance with an embodiment of the present disclosure.

The medical imaging apparatus 10, in the present embodiment the magnetic resonance apparatus 11, further comprises at least one display 100, which is arranged within the examination room 27. In the present exemplary embodiment, the medical imaging apparatus 10, in particular the magnetic resonance apparatus 11, comprises a plurality of displays 100, which are arranged within the examination room 27, wherein only two of the displays 100 are shown in FIG. 2. The embodiment of the medical imaging apparatus 10, in particular the magnetic resonance apparatus 11, however, is not restricted to two displays 100. In an alternative embodiment of the invention, the medical imaging apparatus 10, in particular the magnetic resonance apparatus 11, may also only comprise a single display 100 or any suitable number of additional displays 100 (e.g. three or more displays 100).

For actuating the individual displays 100 arranged in the examination room 27, the medical imaging apparatus 10, in the present embodiment the magnetic resonance apparatus 11 has a master unit 101. The master unit 101 is connected to the computing unit 23. In the present embodiment, the master unit 101 is embodied separately from the computing unit 23. Alternatively, the master unit 101 may also be comprised by the computing unit 23 or be integrated as part of the computing unit 23.

Furthermore, the individual displays 100 arranged in the examination room 27 each have a slave unit 102. Additional details regarding a first embodiment for an arrangement of a master unit 101 and a plurality of slave units 102 of the medical imaging apparatus 10 are shown in FIG. 2.

FIG. 2 shows an example schematic representation of a first arrangement of a master unit and a plurality of slave units, in accordance with an embodiment of the present disclosure. The master unit 101 shown in FIG. 2 is connected to the slave unit 102 of the first display 100 by means of a data connection 103. In the present embodiment, the data connection 103 comprises an optical data connection 103 between the master unit 101 and the slave unit 102 of the first display 100. The data connection 103 comprises a bidirectional data connection 103 between the master unit 101 and the slave unit 102. The optical data connection 103 may comprise, for instance, optical waveguides and/or fiber optic cables, which enable a data transfer and/or a signal transfer between the master unit 101 and the slave unit 102 of the first display 100. This is advantageous in an embodiment of the medical imaging apparatus 10 as a magnetic resonance apparatus 11, since here disruptions to and/or interference in the image data capture may occur during a magnetic resonance examination due to electrical conductors and/or copper conductors, which may generate electric and/or electromagnetic fields.

If, by contrast, the medical imaging apparatus 10 is formed by a further medical imaging apparatus 10 differing from a magnetic resonance apparatus 11, then the data connection 103 between the master unit 101 and the at least one slave unit 102 may also differ from an optical data connection 103. In this context, the data connection 103 may comprise any suitable type of connection in a manner that appears expedient to the person skilled in the art.

The master unit 101 comprises a logic unit 104 and/or a logic circuit/circuitry, such as an FPGA for example, by means of which a transfer protocol (e.g. an HMINet protocol), for actuating the at least one display 100 and, when used, the plurality of displays 100, can be generated. By means of the logic unit 104, it is possible in particular for individual access rights for the individual displays 100, (e.g. the slave units 102 of the individual displays 100), to be regulated by the master unit 101. When generating the transfer protocol (e.g. the optical transfer protocol or an HMINet protocol), standard image data and/or standard image signals are converted into the transfer protocol. The standard image signals may comprise image signals, for example, which may be transferred for example via a USB interface (e.g. USB 2.x, USB 3.x, etc.), via an I2C interface, via a DisplayPort interface, via a LVDS interface, etc.

The master unit 101 furthermore comprises a microcontroller 105, which may be for example for a configuration and/or implementation of the logic unit 104. Furthermore, the master unit 101 includes an Ethernet module 106. The Ethernet module 106 may, for example, comprise an Ethernet connection between, for example, a microcontroller 105 and the logic unit 104, and to a USB interface 107 of the master unit 101. By means of the USB interface 107 in this example, a connection can be established between the master unit 101 and a central host PC 108 of the computing unit 23. By means of the Ethernet module 106, it is possible for an Ethernet-based diagnosis of the master unit 101, for example the logic unit 104 of the master unit 101 to be carried out. It is also possible, by means of the Ethernet module 106, for a network management of the master unit 101 or also of the data connection 103 to the master unit 101 with the individual slave units 102 to be provided. In addition, updates for the individual units of the master unit 101 or also updates for individual units of the displays 100 or slave units 102 can be carried out by means of the Ethernet module 106.

In this context, the USB interface 107 of the master unit 101 may comprise a USB 2.x interface, a USB 3.x interface, etc. In addition, in the present embodiment the master unit 101 also comprises a DisplayPort interface 109. The central host PC 108 of the computing unit 23 is arranged within the control room 28 together with the master unit 101. The central host PC 108 may comprise the user interface 24 with the input unit 26 and the output unit 27. In addition, the central host PC 108 is connected to the master unit 101 by means of the USB interface 107 and by means of the DisplayPort interface 109. In an alternative embodiment, the central host PC 108 is also only connected to the master unit 101 by means of the USB interface 107 or only by means of the DisplayPort interface 109. In addition, further suitable interfaces for connecting the central host PC 108 to the master unit 101, which appear expedient to the person skilled in the art, are readily possible in an alternative embodiments.

By means of the central host PC 108 and the Ethernet module 106, a configuration and/or implementation of the master unit 101 can be carried out. A configuration and/or implementation of the transfer protocol can also be carried out by means of the central host PC 109 and the Ethernet module 106. Furthermore, by means of the central host PC 108 and the Ethernet module 106, a connection diagnosis can take place between the master unit 101 and the displays 100, in particular the slave units 102, and/or between the individual displays 100, in particular the individual slave units 102.

The slave units 102 of the individual displays 100 each comprise a dedicated logic unit 110. The individual logic units 110 may each comprise an FPGA, for instance. By means of the logic units 110, it is possible for the transfer protocol (e.g. the HMINet protocol), which has been transferred from the master unit 101 to the displays 100, to be executed in the respective slave units 102. When executing the received transfer protocol, it is possible for control signals for the individual displays 100 to be generated by the slave units 102 (e.g. the logic units 110 of the slave units 102). In this context, the transfer protocol, can be transferred into standard image signals for display interfaces of the individual displays 100, such as LVDS, I2C, USB, etc., for instance. For example, the LVDS data and/or LVDS signals can be used for an output to and/or actuation of an LCD panel of the displays 100. The I2C data and/or the I2C signals may for example be used for an output to and/or actuation of a touch controller of the display 100, etc. For transferring the standard image signals from the slave units 102 to display interfaces, the slave units each may have an interface 111 for relaying the received control signals and/or display signals.

The master unit 101 furthermore comprises a transceiver unit 112 (e.g., transceiver circuitry) for transferring the transfer protocol to the slave unit 102 of the first display 100.

In addition, the first display 100 also comprises a transceiver unit 113, by means of which data is able to be received from the master unit 110.

The first display 100 additionally comprises a second transceiver unit 114 for connecting to the second display 100. To this end, the second display 100 also has a transceiver unit 113, in order to receive data (e.g. the transfer protocol), from the first display 100. The data for the second display 100 is transmitted from the master unit 101 to the first display 100, and from there transferred to the second display 100. To this end, the data for the first display 100, together with the data for the second display 100, is initially transferred from the master unit 101 to the first display 100 and from there transferred to the second display 100.

Arranged between the slave unit 102 and/or transceiver unit 114 of the first display 100 and the slave unit 102 and/or transceiver unit 113 of the second display 100 is a further data connection 115 of the medical imaging apparatus 10. This data connection 115 is, in this example of the present embodiment, formed by an optical data connection 115. The optical data connection 115 may comprise, for instance, optical waveguides and/or fiber optic cables, which enable a data transfer and/or a signal transfer between the slave unit 102 of the first display 100 and the slave unit 102 of the second display 100.

The data and/or portions of the transfer protocol, for which the slave unit 102 of the first display 100 has access rights and/or has been issued access rights by the master unit 101, are executed by the slave unit 102 of the first display 100. The data and/or portions of the transfer protocol, which are provided for the second display 100 or further displays 100, are looped through on the first display 100 (e.g. the slave unit 102 of the first display 100), for forwarding to the second display 100. The data and/or portions of the transfer protocol, for which the slave unit 102 of the second display 100 has access rights and/or has been issued access rights by the master unit 101, are executed by the slave unit 102 of the second display 100. The data and/or portions of the transfer protocol, which are provided for further displays 100, are likewise looped through on the second display 100 (e.g. the slave unit 102) of the second display 100, for forwarding to the further displays 100.

If, for example, the medical imaging apparatus 10, in particular the magnetic resonance apparatus 11, has more than two displays 100, then the second display 100 also has a second transceiver unit 114, for connecting to the third display 100. The data and/or portions of the transfer protocol, which are provided for the third display 100 or further displays 100, are looped through on the first display 100 (e.g. the first slave unit 102), and also on the second display 100 (e.g. the second slave unit 102), for forwarding to the third display 100. The data and/or portions of the transfer protocol, for which the slave unit 102 of the third display 100 has access rights and/or has been issued access rights by the master unit 101, are executed by the slave unit 102 of the third display 100.

On the basis of the data transfer to the second display 100 via the first display 100, an operating mode and/or operating state of the second display 100 (and also of further displays 100) is thus at least partially dependent upon an operating mode and/or operating state of the first display 100. If the first display 100 is situated in a switched-on operating state and/or operating mode, it is possible for data to be transferred to the second display 100 or the further displays 100.

The second display 100 and the third display 100 (or also further displays 100) are embodied similarly to the description above. However, for purposes of clarity, the second display is outlined in a high-level and a third display 100 is indicated only on the basis of the second transceiver unit 114 of the second display 100.

More generally speaking, the following relationship results between the individual displays 100 of the medical imaging apparatus 10:

If the medical imaging apparatus 10 comprises n displays 100, where n≥2, then in this context the (n−1)th display 100 comprises a transceiver unit 114 for a data connection to the n-th display 100. Here, each (n−1)th display 100 comprises a first transceiver unit 113 for input and/or receiving of the transfer protocol, and a second transceiver unit 114 for forwarding the transfer protocol to the n-th display 100. In this context, an operating mode of the n-th display 100 is also at least partially dependent upon an operating mode of the (n−1)th display 100. In the embodiment shown in FIG. 2, n≥2.

Figure 3:
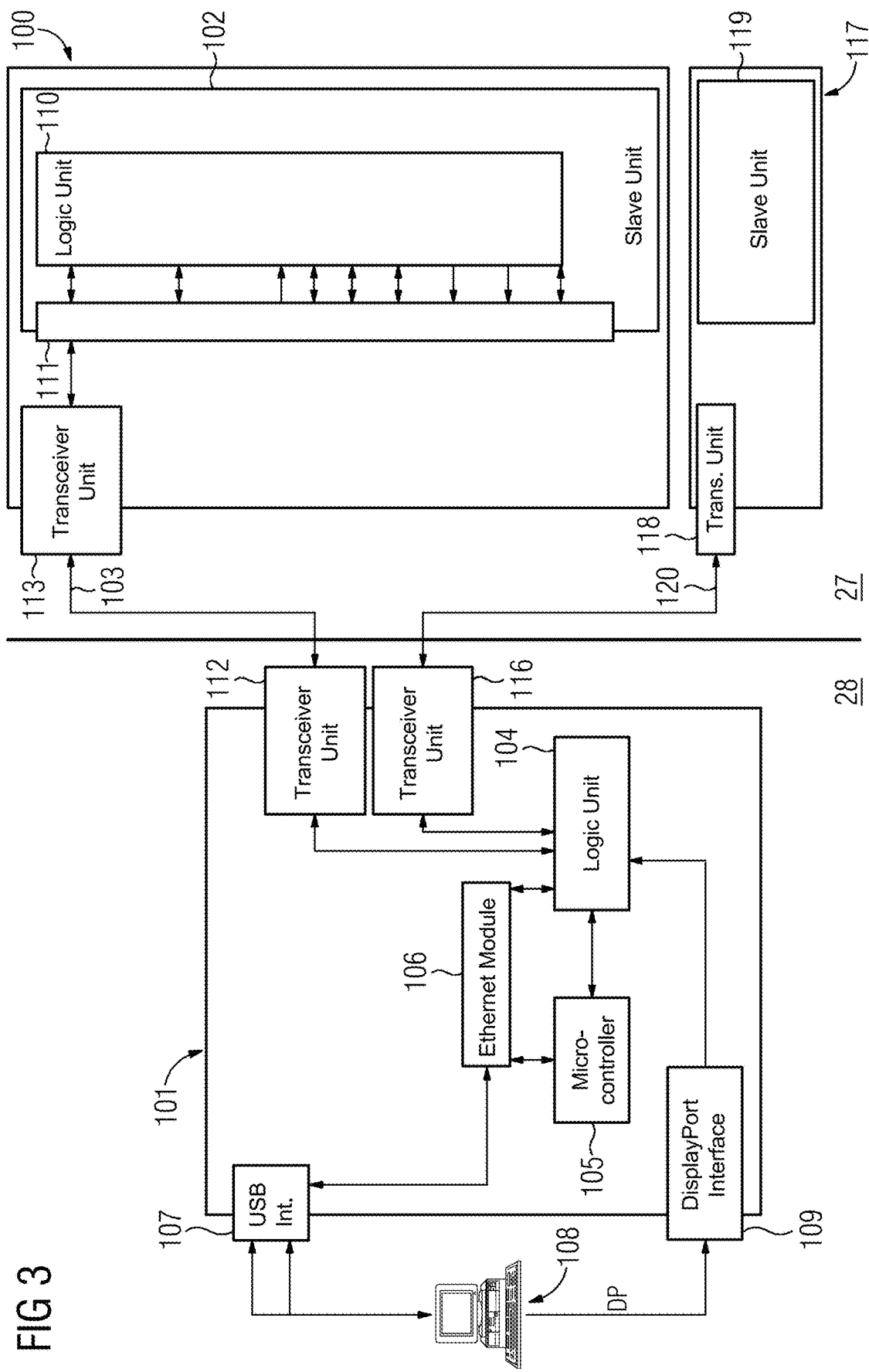
FIG. 3 shows an example schematic representation of a second arrangement of a master unit and a plurality of slave units, in accordance with an embodiment of the present disclosure.

FIG. 3 shows an example schematic representation of a second arrangement of a master unit and a plurality of slave units, in accordance with an embodiment of the present disclosure. FIG. 3 shows an alternative exemplary embodiment of the master unit 101. In principle, components, features and functions remaining substantially the same are identified with the same reference characters. Thus, in the following description only the differences from the embodiment as shown in FIG. 2 are further described, with reference being made to the description of the exemplary embodiment in FIG. 2 in respect of components, features and functions that remain the same.

As shown in FIG. 3, the master unit 101 has two transceiver units 112, 116. The first transceiver unit 112 is provided for transferring the transfer protocol to the slave unit 102 of the first display 100. The second transceiver unit 116 is provided for transferring a transfer protocol to a further unit 117, which in the present embodiment comprises a USB interface. Preferably, the USB interface (e.g. a USB 3.x interface) for linking to a USB device (e.g. a device with a USB interface). As an alternative, the further unit 117 may also comprise a further display.

In the present exemplary embodiment, the further unit 117 likewise has a transceiver unit 118 and a slave unit 119. The further unit 117 is likewise connected to the master unit 101 via a data connection 120. Here, the data connection 120 is arranged between the transceiver unit 116 of the master unit 101 and the transceiver unit 118 of the further unit 117. The data connection 120 may, in the present exemplary embodiment, be formed by an optical data connection 120, which may include optical waveguides and/or fiber optic cables, for example, and which enable a data transfer and/or a signal transfer.

An arrangement of the plurality of displays 100, which are connected to the first transceiver unit 112 of the master unit 101 via the data connection 103, is embodied similarly to the description of FIG. 2, although this is indicated by the representation of one display 100 in FIG. 3.

The medical imaging apparatus 10 shown, including the magnetic resonance apparatus 11, may of course comprise further components, which medical imaging apparatuses 10, including magnetic resonance apparatuses 11 usually have. A general mode of operation of a medical imaging apparatus 10, in particular the magnetic resonance apparatus 11, is also known to the person skilled in the art, so that a detailed description of the further components will be dispensed with.

Figure 4:
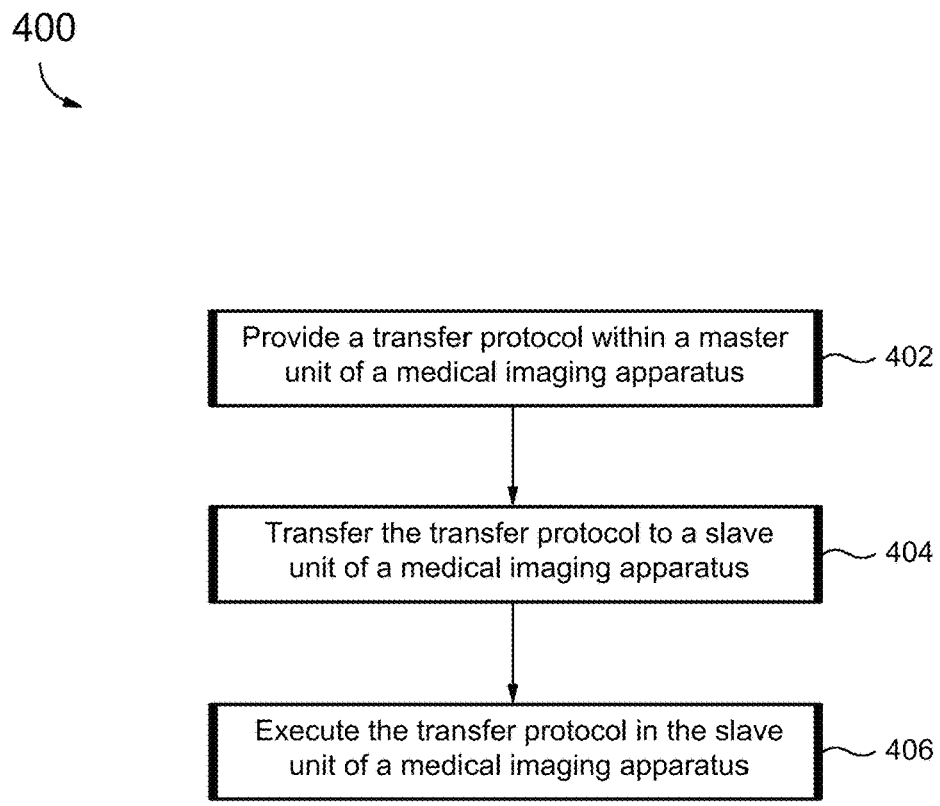
FIG. 4 shows an example method for actuating at least one display of a medical imaging apparatus, in accordance with an embodiment of the present disclosure.

FIG. 4 shows an example method for actuating at least one display of a medical imaging apparatus, in accordance with an embodiment of the present disclosure. FIG. 4 shows a method 400 according to the disclosure for actuating at least one display 100 of the medical imaging apparatus 10. The medical imaging apparatus 10, e.g. the magnetic resonance apparatus 11, may be embodied in accordance with the embodiments of FIGS. 1 to 3 shown above. Moreover, the method 400 may be executed via one or more processors associated with the medical resonance apparatus 11, as shown and discussed herein with reference to FIG. 1, for instance. As an illustrative example, the method 400 may be executed via the computing unit 23, as shown in FIG. 1.

The method 400 may begin by providing (block 402) the transfer protocol within the master unit 101 of the medical imaging apparatus 10. The method may include transferring (block 404) the transfer protocol to the slave unit 102 of the first display 100 by means of the data connection 103. The method 400 may further include executing (block 406) the transfer protocol in the slave unit 102 of the first display 100.

Again, if the transfer protocol has data for the first display 100 and for further displays 100, then the data for the further displays 100 is also transferred from the master unit 101 to the first display 100, in particular to the slave unit 102 of the first display 100, and from there transferred to the further displays 100 (e.g. the slave units 102 of the further displays 100), in block 404. The data and/or portions of the transfer protocol, which are provided for further displays 100, in in block 404 may also be looped through the first display 100 (e.g. in the slave unit 102) of the first display 100, for forwarding to the further displays 100.

It is additionally possible for the provided transfer protocol to be carried out, on the basis of the Ethernet module 106 of the master unit 101, for an Ethernet-based evaluation of the connection between the master unit 101 and the slave units 102 (or also between the individual slave units 102). In addition, it is also possible for an Ethernet-based network management to be carried out.

By means of the computing unit 23 of the medical imaging apparatus 10, such as the magnetic resonance apparatus 11, it is additionally possible for an automatic shutdown of the individual displays 100 to take place. For instance, the automatic shutdown of individual displays 100 may occur place during a medical imaging examination, such as during a magnetic resonance examination, for example.

Although the embodiments of the present disclosure have been illustrated and described in detail using the preferred exemplary embodiment, the disclosure is not limited by the disclosed examples, and a person skilled in the art can derive other variations therefrom without departing from the scope of protection of the disclosure.

What is claimed is:

1. A medical imaging apparatus, comprising:
a data acquisition scanner configured to acquire medical imaging data during a medical imaging scan;
a control computer;
master circuitry coupled to the control computer, the master circuitry comprising master logic circuitry configured to convert image signals received via the control computer to generate transfer protocol data that includes pixel data; and
at least one display comprising
slave circuitry, the slave circuitry comprising slave logic circuitry configured to execute the transfer protocol data such that the at least one display is off during the medical imaging scan, and the at least one display presents images identified with the converted image signals when the medical imaging scan is not being performed due to display actuation via the pixel data, and wherein the master circuitry is connected to the slave circuitry via a data connection associated with the medical imaging apparatus.

2. The medical imaging apparatus as claimed in claim 1, wherein the data connection comprises an optical data connection between the slave circuitry and the master circuitry.

3. The medical imaging apparatus as claimed in claim 2, wherein the data connection comprises a bidirectional data connection.

4. The medical imaging apparatus of claim 1, wherein the data acquisition scanner comprises a magnetic resonance data acquisition scanner.

5. The medical imaging apparatus of claim 1, wherein the master logic circuitry is configured to generate the transfer protocol data to regulate access rights to the transfer protocol data via the slave circuitry of the at least one display.

6. The medical imaging apparatus of claim 1, wherein:
the master logic circuitry comprises a field programmable gate array (FPGA);
the slave logic circuitry comprises a field programmable gate array (FPGA).

7. The medical imaging apparatus of claim 1, wherein the transfer protocol data is transmitted in accordance with a Human Machine Interface Net (HMINet) protocol.

8. The medical imaging apparatus as claimed in claim 1, wherein the slave circuitry of the at least one display includes an interface for relaying received control signals and/or display data to another device.

9. The medical imaging apparatus as claimed in claim 1, wherein the at least one display includes a first transceiver and the master circuitry includes a second transceiver.

10. The medical imaging apparatus as claimed in claim 1, wherein the at least one display includes a first display and second display, and
wherein the slave circuitry includes the second display.

11. The medical imaging apparatus as claimed in claim 1, wherein the at least one display is from among a plurality of displays that includes at least a first display and a second display, and
wherein the first display includes a transceiver to enable a data connection to the second display.

12. The medical imaging apparatus as claimed in claim 11, wherein each display from among the plurality of displays includes a first transceiver configured to input a transfer protocol data and a second transceiver configured to forward the transfer protocol data.

13. The medical imaging apparatus as claimed in claim 11, wherein an operating mode of the second display is at least partially dependent upon an operating mode of the first display.

14. The medical imaging apparatus as claimed in claim 1, wherein the master circuitry includes a first transceiver configured to transfer the transfer protocol data to the at least one display and a second transceiver configured to transfer a further transfer protocol data to another slave circuitry.

15. The medical imaging apparatus as claimed in claim 1, wherein the master circuitry includes an Ethernet connection.

16. The medical imaging apparatus as claimed in claim 1, further comprising:
a central host PC arranged within a control room with the master circuitry.

17. The medical imaging apparatus as claimed in claim 16, wherein the master circuitry includes at least one data interface and/or at least one graphical interface configured to exchange data with the central host PC.

18. A method for actuating at least one display of a medical imaging apparatus that includes a control computer, a master circuitry coupled to the control computer, and at least one display, the method comprising:
generating, via the master circuitry, transfer protocol data that includes pixel data resulting from a conversion of image signals received via the control computer;
transferring, via one or more processors using a data connection, the transfer protocol data to slave circuitry of the at least one display; and
executing, via the slave circuitry, the transfer protocol data such that the at least one display is off during a medical imaging scan performed via the medical imaging apparatus, and the at least one display presents images identified with the converted image signals when the medical imaging scan is not being performed due to display actuation via the pixel data.

19. The method as claimed in claim 18, wherein:
the transfer protocol data comprises data for a first display and data for at least one further display,
the data for the at least one further display is transferred from the master circuitry to the slave circuitry of the first display, and
the data is further transferred from the slave circuitry of the first display to slave circuitry of the at least one further display.

20. The method as claimed in claim 18, further comprising:
performing an Ethernet-based evaluation of a data connection between the master circuitry and the at least one display and/or an Ethernet-based network management.

* * * * *